US006356205B1

United States Patent
Salvo et al.

(10) Patent No.: US 6,356,205 B1
(45) Date of Patent: Mar. 12, 2002

(54) MONITORING, DIAGNOSTIC, AND REPORTING SYSTEM AND PROCESS

(75) Inventors: Joseph James Salvo, Schenectady; Patricia Denise Mackenzie, Clifton Park, both of NY (US)

(73) Assignee: General Electric, Schenectady, NY (US)

( * ) Notice: Subject to any disclaimer, the term of this patent is extended or adjusted under 35 U.S.C. 154(b) by 0 days.

(21) Appl. No.: 09/201,385

(22) Filed: Nov. 30, 1998

(51) Int. Cl.$^7$ ............................................. G01N 27/00
(52) U.S. Cl. ............................... 340/853.3; 340/853.2; 340/870.07; 73/152.18; 73/152.29; 210/143; 702/23
(58) Field of Search ........................ 340/853.2, 853.3, 340/870.07; 324/357, 345; 367/39, 57, 86; 166/250.1; 73/152.29, 152.19; 422/82.09, 82.05; 702/23; 210/143

(56) References Cited

U.S. PATENT DOCUMENTS

| | | | | |
|---|---|---|---|---|
| 4,973,970 A | * | 11/1990 | Reeser | 342/357 |
| 5,120,160 A | * | 6/1992 | Schwengel | 405/128 |
| 5,283,767 A | | 2/1994 | McCoy | 367/4 |
| 5,543,623 A | * | 8/1996 | Everett | 250/390.04 |
| 5,553,492 A | * | 9/1996 | Barrett | 73/152.29 |
| 5,629,626 A | * | 5/1997 | Russell et al. | 324/345 |
| 5,646,863 A | * | 7/1997 | Morton | 364/496 |
| 5,687,093 A | * | 11/1997 | Long | 364/512 |
| 5,808,916 A | * | 9/1998 | Orr | 364/578 |
| 5,824,270 A | * | 10/1998 | Rao | 422/82.09 |
| 5,825,188 A | * | 10/1998 | Montgomery | 324/357 |
| 5,942,440 A | * | 8/1999 | Dooley | 436/146 |
| 5,963,508 A | * | 10/1999 | Withers | 367/38 |

FOREIGN PATENT DOCUMENTS

| | | |
|---|---|---|
| DE | 19626262 A1 | 1/1998 |
| FR | 2 689 639 | 10/1993 |
| WO | WO 96/25726 | 8/1996 |

OTHER PUBLICATIONS

Services & Systems, NTT Review, "New Multimedia Communication Services using Sensing Systems", Development of Water–Quality Sensing Network System, Kuwano, Hiroki, Katoh, Tadashi, Yasuda, Kyousuke and Watanabe, Toshio, pp. 100–107, vol. 9, No. 1 (Jan. 1997).
Envirex, Co., Fluid Bed News, Apr. 1994.
YSI Inc., WQ Monitor, vol. 8, Issue 1, 1998.
John Callanan, "Low–Hassle, Low–Cost Leak–Detection," The Journal of Petroleum Marketing, Nov. 1996, reprint.
"System Delivers Information Management in 'Real–Time'," Elements, vol. 26, No. 2, 1997, p. 2.
"All–weather water quality monitor," Environmental Science & Technology/News, p. 85 Feb. 1, 1998.
"Remote Access Process Control Technology Increases Efficiency," GWMR, p. 160, Spring 1997.
"The Microtox–OS Test System," AZUR Environmental.
"Protecting wastewater treatment processes," Model GWM–2000, Water/Oil Interface Tracking System, USD Bulletin No. GSM–9501.

* cited by examiner

Primary Examiner—Michael Horabik
Assistant Examiner—Albert K. Wong
(74) Attorney, Agent, or Firm—Toan P. Vo; Noreen C. Johnson

(57) ABSTRACT

A monitoring system determines characteristics of a fluid in a well. The system comprises a well module adapted to be disposed in a well, where the module comprises a probe and at least one sensor that senses characteristics of the fluid. The well module is capable of transmitting information concerning fluid characteristics. The system further comprises a data collection center, which is capable of receiving well information from the well module and generating information concerning characteristics of the fluid, a monitoring site, and a communication link that enables a user at the monitoring site to obtain information such as, but not limited to, real-time, historical, and a combination of real-time and historical concerning the characteristics.

44 Claims, 5 Drawing Sheets

MONITORING, DIAGNOSTIC, AND REPORTING SYSTEM AND PROCESS

BACKGROUND OF THE INVENTION

The invention relates to remote monitoring, diagnostic, and reporting methods and systems. In particular, the invention relates to remote monitoring, diagnostics, and reporting methods and systems for water; for wells; and for groundwater monitoring at remediation sites.

Conventional remediation site monitoring, diagnostics, and reporting are expensive and labor intensive operations. Yearly costs for remediation site monitoring, diagnostics, and reporting often exceed over about $2000 per well. Conventional remediation site monitoring, diagnostics, and reporting methods and systems comprise providing a well or other access means for groundwater at a remediation site. A person visits the remediation site, locates the well, and accesses the well. The groundwater in the well is sampled for characteristics (hereinafter "groundwater characteristics"), such as, but not limited to, contaminants; water quality parameters; groundwater level; and impurities, including benzene, toluene, chlorinated solvents, ethylbenzene, aromatic hydrocarbons, xylenes (BTEX) in the groundwater. The groundwater sample is then transported to a laboratory, often remote from the remediation site. The sample is then analyzed for certain characteristics by appropriate methods. Costs are associated with each step, and the costs are often high depending on the well's location with respect to the laboratory. Exact costs are remediation site dependent, reflecting a complexity of an analysis to be performed.

Real-time data for the groundwater is not available. The transportation of the sample from the well to the laboratory takes time. Further, time delays are associated with the analysis of the groundwater sample. Thus, when results of the groundwater analysis are available for study, a long period of time may have passed. Any actions necessitated, recommended, or required by the groundwater analysis may not be accurate, and may be detrimental, as the remediation site groundwater its characteristics may have been altered, typically permanently, over the time from sampling to analysis.

Therefore, an alternative method and system for conventional sampling and laboratory analysis are needed. A remote monitoring, diagnostics, and reporting system and method both provide real-time data. The real-time data can be analyzed at the remediation site so that prompt action can be taken addressing the groundwater characteristics.

SUMMARY OF THE INVENTION

The invention overcomes the above noted deficiencies of known monitoring methods and systems. The invention provides for a monitoring system that determines fluid characteristics in a well. The system comprises a well module adapted to be disposed in a well, in which the module comprises a probe and at least one sensor that senses characteristics of the fluid in the well. The well module is capable of transmitting information concerning fluid characteristics. The system further comprises a data collection center, which is capable of receiving well information from the well module and generating information concerning characteristics of the fluid; a monitoring site; and a communication link that enables a user at the monitoring site to obtain information concerning the fluid characteristics.

The invention also sets forth a method of monitoring fluid characteristics of a well. The method comprises disposing an well module in a well, the module comprising a probe and at least one sensor; sensing fluid characteristics, transmitting information concerning fluid characteristics to a data collection center; receiving information concerning fluid characteristics at the data collection center; generating information concerning fluid characteristics at the data collection center; and obtaining information concerning the fluid characteristics at a monitoring site.

These and other aspects, advantages and salient features of the invention will become apparent from the following detailed description, which, when taken in conjunction with the annexed drawings, where like parts are designated by like reference characters throughout the drawings, disclose embodiments of the invention.

DETAILED DESCRIPTION OF INVENTION

The invention provides a remote monitoring, diagnostics, and reporting system and method (hereinafter "monitoring system"), for example, but in no way limiting of the invention, for monitoring groundwater at remediation sites. The monitoring system reduces costs associated with known monitoring systems and methods. The monitoring system and method, as embodied by the invention, provide real-time and historic data through remote monitoring, diagnostics, and reporting of desired characteristics to a user.

The invention is described herein with respect to groundwater characteristics at a groundwater well. This description is exemplary and is not meant to limit the invention in any way. The monitoring system can be used to determine characteristics in other environments, including, but not limited to, fluid flow at airports (including, but not limited to, glycol runoff), land fills, aquifers, sewer and sewerage systems, and other aqueous environments. Further, the monitoring system can be used to determine spill flow and assist in spill control to control discharges of undesirable materials.

Figure 1:
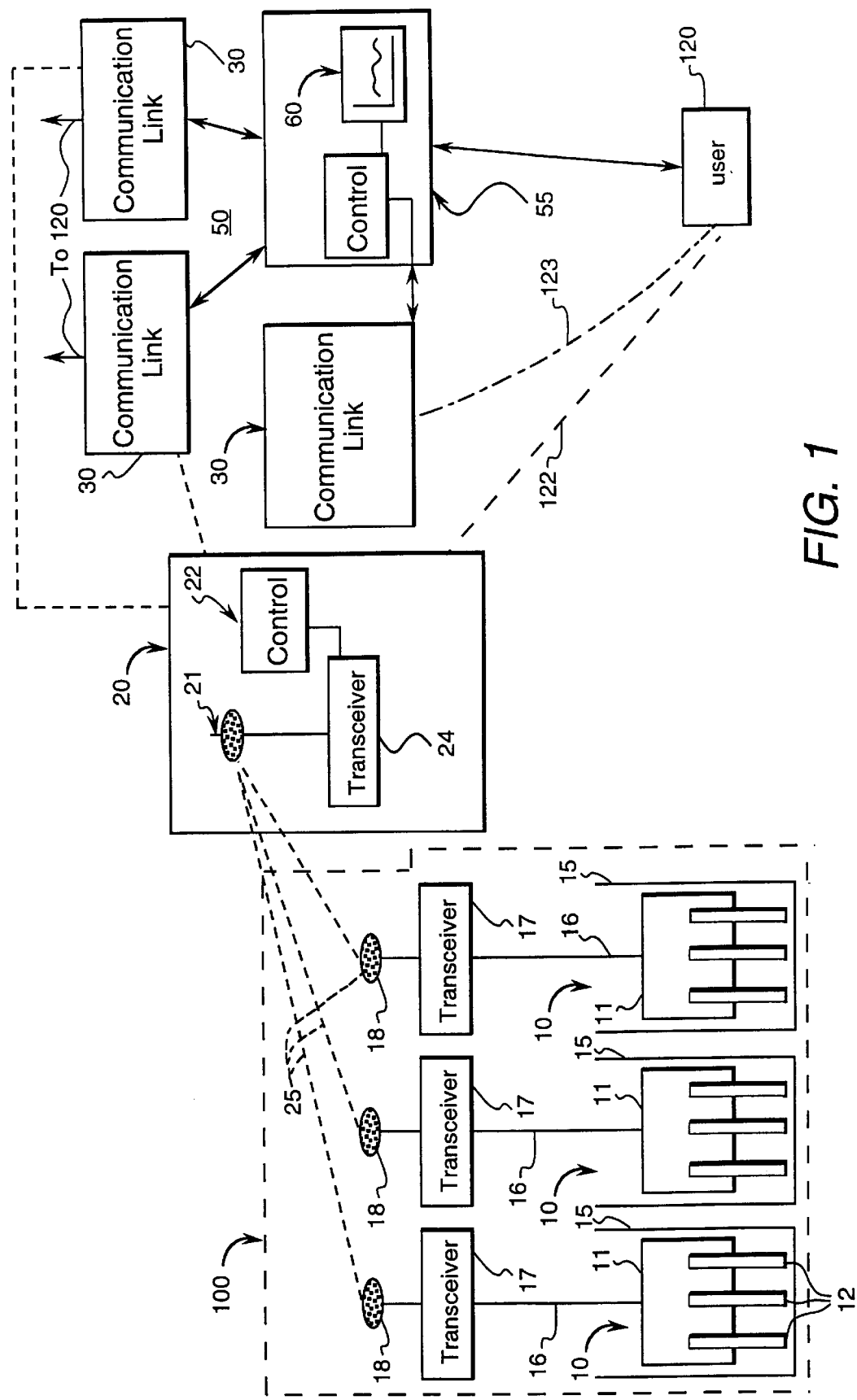
FIG. 1 is a schematic illustration of a remote monitoring, diagnostics, and reporting system.

The monitoring system 1 is schematically illustrated in FIG. 1. The monitoring system 1 comprises a well module (module) 10. The module 10 comprises a probe 11 and at least one sensor 12 disposed on the probe 11. FIG. 1 illustrates three (3) such sensors 12, however this is merely exemplary and is not meant to limit the invention in any way. The module 10 includes any number of sensors 12 whereby desired groundwater characteristics are readily determined.

The module 10 is disposed in groundwater wells 15 at a remediation site 100. Groundwater wells 15 include, but are not limited to, private drinking water wells, municipal drinking water wells, pollution control wells, and landfill monitoring wells. The wells 15 can be spread throughout a remediation site 100 or over a larger or smaller area, for example disposed in varying altitudes to determine groundwater flow characteristics. The module 10 generates signals (data) corresponding to one or more of the groundwater characteristics. The module 10 includes a communications unit 19, which is electronically coupled and capable of transmitting data to a data collection center 20 (to be described hereinafter). The communications unit 19 includes a well transceiver 17 to which signals from the module 10 are communicated to a data collection center 20. The communication unit 19 need not be a high power unit if the center 20 is near the well 15, and supplies power suitable to transfer information. The signals are communicated, for example from well transceiver 17 to the data collection center 20, by at least one of a hardwired communication connection, such as, but not limited to, an electrical conductor 16; wireless communication connections, such as, but not limited to, radio signals, satellite communications; and combinations of wireless and hardwired connections. The communications unit 19 also typically comprises an antenna 18 that is connected to the transceiver 17, unless the communications unit 19 is hardwired. The transceiver 17 transmits information in the form of signals 25 representative of the data from the communications unit 19 to a data collection center 20.

The data collection center 20 comprises a center communications unit 21 that receives the signals 25 from the transceiver 16. The center communications unit 21, which is similar to the communications unit 19, typically comprises an antenna 23 (which is not needed if hardwired) and a transceiver 24. If more than one well is located at the remediation site 100, the center communications unit 21 is capable of receiving signals 25 from a plurality of wells 15 at the remediation site 100. The data collection center 20 also comprises a control 22 that analyzes the signals 25 and typically generates information concerning the groundwater characteristics. The control 22 of the data collection center 20 typically includes a "user friendly" data acquisition software package. The software package in the control 22 transforms information into easy to read formats.

The information transmitted to the data collection center 20 contains data representative of the groundwater characteristics. The information is collected and can be stored at the data collection center 20. The information can be accessed by a user, regardless if the user is located at the data collection center 20 or remote therefrom (as described in detail hereinafter). The information format structure can be customized by the user, where the user formats a desired information structure in a report dependent on the intended use of the information. The information is formatted to interpret, classify, quantify, and categorize the groundwater characteristics. For example, but in no way limiting of the invention, the information reports provide real-time information concerning groundwater characteristics. The information reports are also can be formatted to provide a historical summary for the groundwater characteristics of the individual wells 15 and the remediation site 100.

The data collection center 20 is typically located proximate a well 15 so the communication unit 19 transmits signals with sufficient strength so the data collection center 20 can receive them. For example, the data collection center 20 is located at the remediation site 100 within range of the communication unit 19. Alternatively, the data collection center 20 is located proximate a remediation site 100, such as, but not limited to, adjacent one or more remediation sites 100 so the data collection center 20 can receive data from each communication unit 19. In an alternative, the data collection center 20 is mobile and can be moved within range of the communication unit 19 to receive data. The location of the data collection center 20 is typically anywhere within range of the communication unit 19.

The control 22 comprises any appropriate solid-state device, for example a computer. The control center 22 may include data acquisition capability, such as data acquisition software. This configuration is merely exemplary of an appropriate high-powered control, which is within the scope of the invention. A control 22 alternatively comprises a central processor for overall, system-level control, and separate sections performing various different specific combinations, functions and other processes under control of the central processor section are also within the scope of the invention. It will be appreciated by those skilled in the art that the control 22 can also be implemented using a variety of separate dedicated, programmable integrated, and other electronic circuits or devices. These devices include hardwired electronic, logic circuits including discrete element circuits, and programmable logic devices. The programmable logic devices include at least one of a programmable logic device (PLD), programmable array logic (PAL), programmable logic array (PLA) and the like. The control can also be implemented using a suitably programmed general-purpose computer, such as, but not limited to, a microprocessor, microcontrol, or other processor device, for example at least one control processing unit (CPU) and microprocessing unit (MPU), either alone or in conjunction with one or more peripheral data and signal processing devices. In general, any device or similar devices on which a finite state machine capable of implementing the flow charts, as illustrated in the application, can be used as the control.

The control 22 is typically accessible by a user 120 monitoring groundwater characteristics. For example, the control 22 prints out hard copies of the reports and provides electronic outputs that can be read by computers. Alternatively, if the user 120 is located at a central hub monitoring site 50 (hereinafter "monitoring site") remote from the remediation site 100, the user accesses and obtains electronic information corresponding to the groundwater characteristics at the remediation site 100. A user 120 may connect to the data collection center 20 via the monitoring site 50, as illustrated by the solid line 121 in FIG. 1. Alternatively, the user 120 may connect to the data collection center 20 directly, as illustrated by the dashed line 122 in FIG. 1. As another alternative, the user 120 may connect to the data collection center 20 through the communications link 30, as illustrated by the dotted line 123 in FIG. 1. Moreover, a plurality of users may connect to the monitoring site 50 for data from the data collection center 20 through respective communications links 30. The above alternatives are merely exemplary of the invention, and are not meant to limit the invention in any way.

The monitoring site user 120 may receive electronic information from a plurality of remediation sites. The monitoring site 50 communicates with each data collection center 20 through a communication link 30, and may communicate with a plurality of data collection centers 50. The communication link 30 includes, but is not limited to, at least one of a phone modem, network connection, communication, radio communication and other wireless communication systems, cellular communication, satellite communication, web access communication, and Internet access communication, and combinations thereof. The particular construction of the communication link 30 depends on communication link types accessible at the data collection center 20, remediation site 100, and to the user at the monitoring site 50. The user accesses and readily determines groundwater characteristics from virtually any location via the communication link 30.

The monitoring site 50 need not be a static location, and can be anywhere a user has access to the communication link 30, for example with a web hook-up. The monitoring site 50 comprises a control 55, similar to control 22. The control 55 typically includes a "user-friendly," data acquisition software package, which does not require in-depth knowledge computers. The software package is typically one that transforms information into a formatted report 60 (hereinafter "report"). The report 60 typically includes, but is not limited to, plots, graphs, tables, spreadsheets, and reports. The report 60 is made electronically available to the user, and can be printed as hard copy. Thus, the user does not physically interact with the remediation site 100, nor the well 15, during the gathering of groundwater characteristics. The user merely specifies a report format, and then accesses the data collection center 20 over the communications link 30, and receives the report.

Figure 2:
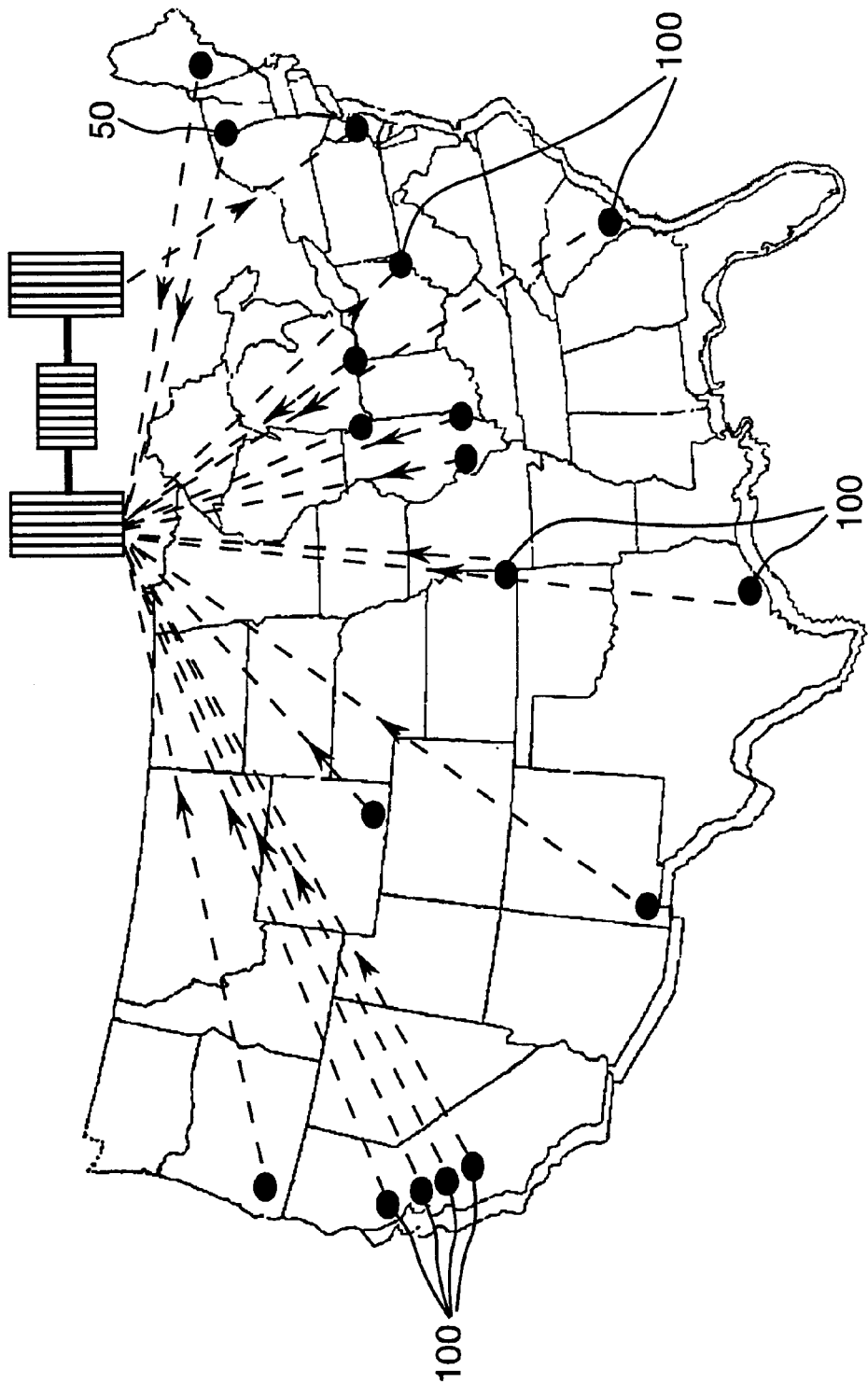
FIG. 2 is an illustration of a system for collection from remediation sites throughout the United States.

A monitoring site 50 is capable of collecting information from remediation sites throughout the country. The monitoring site 50 can be located in a range between a relatively short distance from the data collection center 20, such as less than about 10 meters, and a long distance, such as half way around the world, depending on the range of a communication unit 19. FIG. 2 is an exemplary illustration of a monitoring system 1 for collecting information from remediation sites 100 throughout the United States. A satellite 75 is positioned in geosynchronous orbit over the United States. Although FIG. 2 illustrates a single satellite 75, the invention includes one or more satellites with a monitoring system 1. Information is transmitted over a communications network system, such as a satellite 75. The information is redirected to a monitoring site 50, for example by at least one of bouncing information off a satellite, collection and re-transmission of information, and other similar methods, and is accessible by a network type connection.

Typically, the monitoring system 1 electronically provides at least one of historical and real-time information that is accessible by the user. The user does not require knowledge of specific programs, routines, and customized software packages to access the information because a report is provided in a format of the user's choosing. The user's report format provides information that is usable, easily understood, and manipulatable. The report format provides real-time information, and historical trend analysis (if desired), of groundwater and groundwater characteristics. The real-time information permits quicker responses to undesirable groundwater characteristics, such as a rise in groundwater contaminants.

The monitoring system 1 typically reduces monitoring and reporting costs at remediation sites and provides enhanced, readily available data more frequently, as compared to known monitoring systems. A report 60 may be automatically provided at regular intervals that vary depending on needs of a user, and the nature of the wells, groundwater, remediation site, and contaminants. The intervals include, but are not limited to, once an hour, once every three, four, six and twelve hours, once a day, once every other day, once a week and once a month. This automatic report provision reduces labor intensive sampling at remediation sites 100, and costs associated with transportation of sample, and analysis at analytical laboratories.

The monitoring system 1 generally senses various groundwater characteristics, such as, but not limited to, water quality parameters; groundwater level; and contaminant and impurity content. Exemplary impurities, which may also be considered as contaminants in some instances, include benzene, toluene, chlorinated solvents, ethylbenzene, xylenes (BTEX) in the groundwater.

The monitoring system 1 typically eliminates labor costs and potential errors associated with sampling the well 15. The monitoring system 1 also eliminates sample disposal and associated hazardous material issues; and eliminates both transportation samples for analysis and potential chain of custody issues for contamination sources. Further, the monitoring system 1 substantially eliminates external analytical lab services, reduces remediation site traffic, and potential contamination from the remediation site traffic.

The monitoring system 1 comprises a modular component system, meaning that the individual features of the system 1 are readily interchangeable, replaceable, and adapted for implementation at wells at any remediation site. For example, the module 10 is not specifically sized, shaped, or formed for a particular groundwater well. A sensor 12 can be replaced with a sensor that detects another groundwater characteristic. Alternatively, additional sensors can be added to the module 10, so the module 10 detects additional groundwater characteristics.

The size of the module 10, including the probe 11 and associated sensors 12, permits insertion into most typical groundwater wells. Any type and number of sensors, including vapor and fluid sensors, can be included in the probe 11. As new sensors are developed, they are readily and quickly integrated into the system 1 because of the probe's modular component design. Therefore, the monitoring system 1 does not require additional modification for future use. The probe 11 is disposed in wells to sample at least one of groundwater and groundwater vapor. The probe 11 typically minimizes groundwater purging so only minor amounts of water and silt in the well are disturbed, so as not to cause further contamination. Thus, any harmful materials in the well are not stirred up and further released.

The sensors 12 typically detect the groundwater contaminants of interest at a contaminant level of interest. The sensors 12 are provided in the probe 11 for particular contaminants, and are generally not influenced by other contaminants and matter in the groundwater. The sensors 12 are desirably robust, have a long life, and are non-fouled by groundwater. Types of sensors 12 within the scope of the invention include, but are not limited to, chemical sensors, fiber optics sensors, solid-state sensors, such as, but not limited to, metal oxide sensors, and electrochemical sensors, and combinations thereof. For example, but in no way limiting of the invention, a sensor 12 detects levels of less than about 5 parts per billion (ppb), if this is a desired contaminant sensitivity level. A level sensor, however, may only be fairly sensitive, for example providing a groundwater level within ±1 inch (2.54 cm). The exact degree of sensor sensitivity is dependent on an ultimate intended use of a monitoring system, type of sensor, and degree of exactness desired in the reports.

Each transceiver 17 and 24 of the communications units, 19 and 21, respectively, comprises appropriate devices that receive and send electric signals. Each antenna 18 and 23 (provided unless each transceiver is hardwired) typically comprises an integrated receiver and transmitter antenna. Alternatively, an antenna comprises a separate element from its transceiver. Each transceiver is a low (few volts) power consumption transceiver unit that requires little human interaction. For example, and in no way limiting of the invention, each transceiver uses a self-contained power source, such as at least one of battery packs, solar-power; and solar-power re-charged batteries. Transceiver batteries, if provided, have an extended life, for example, a nickel-cadmium battery that supplies power for extended periods of time. The transceiver saves battery life, as it "sleeps" and is programmed to "wake" and send signals, thus extending its battery life.

Transceiver 17 typically operates without user interaction, and comprises a device that withstands environments of the groundwater well and remediation site, while maintaining its operability. For example, and in no way limiting of the invention, the transceiver 17 comprises one of a radio and RF device that provides coverage over an intended geographical range, such as abandoned industrial waste sites. The transceiver 24 may require more power than the transceiver 17 since it may communicate over longer distances through the communication link 30.

The communication link 30 can provide two-way communication between the user and the module 10. The two-way communication, for example, allows remote monitoring system calibration by a user, without traveling to the site. Also, the two-way communication permits selection, activation and de-activation, modification, fine-tuning, manipulation of the monitoring system 1, and resetting of the control 22 by a user at any monitoring site 50. The two-way communication is provided by any appropriate communication mode, for example, but not limited to email, radio, satellite, facsimile, hardwired communications, voice mail, alarms, mail, and combinations thereof. For example, and in no way limiting of the invention, if the remediation site 100 is provided with groundwater flow control devices, such as pumps, the communication link 30 permits operation and control of the pumps. Therefore, if control of groundwater and groundwater contaminants is desired, the pumps can be actuated by a user from a monitoring site 50 to move groundwater. This remote site pump control by a user prevents groundwater contaminants from flowing into bodies of water or aquifers, which is undesirable, and does not typically necessitate service and maintenance visits to the remediation site.

A user can further transmit the reports and information to others for analysis, review, and archiving. For example, if a well 15 or remediation site 100 is subject to monitoring by regulators, the information can be electronically sent by a user, or automatically to regulators, without generation of paper reports.

Figure 3:
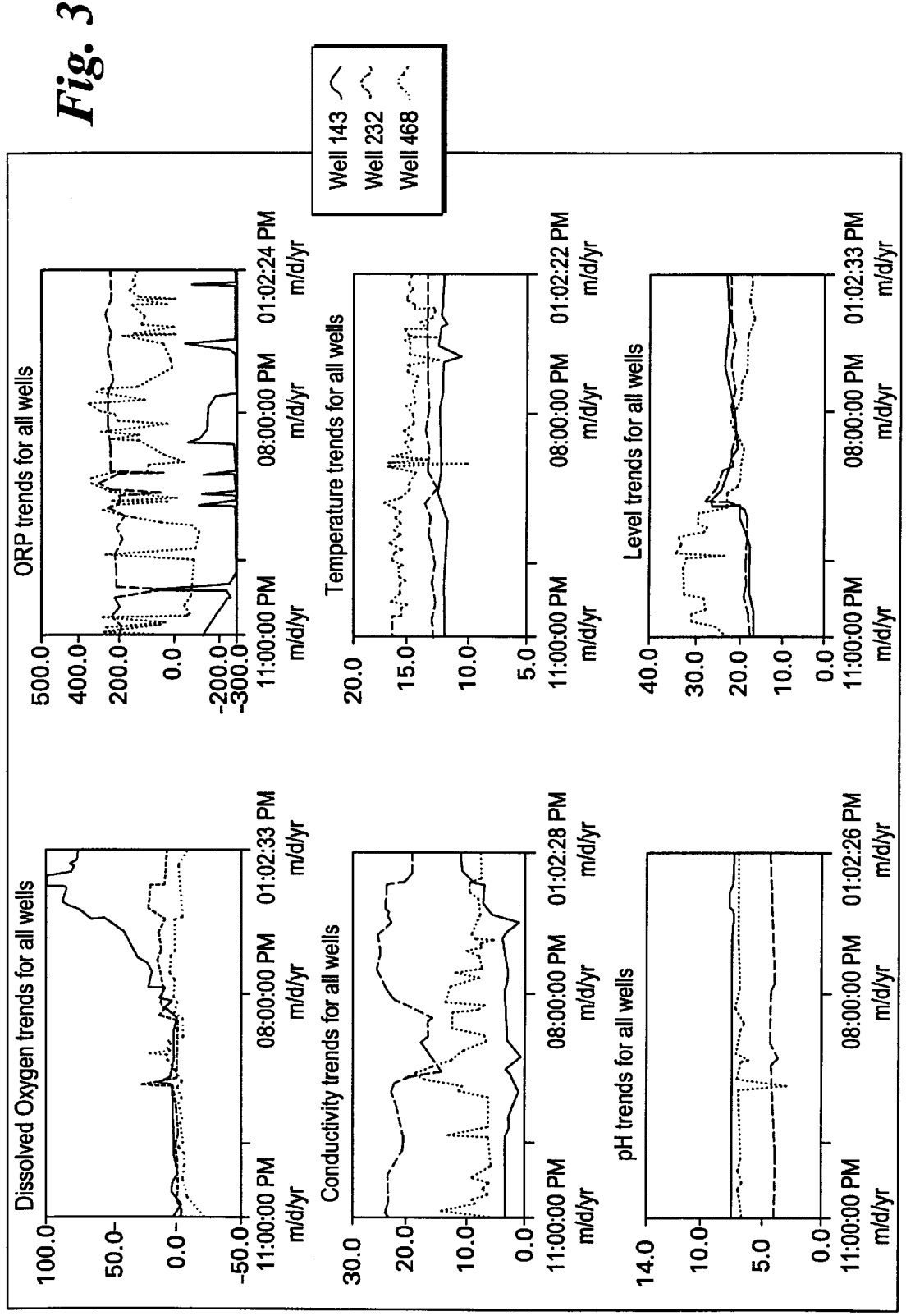
FIGS. 3–5 are exemplary illustrations of report formats.
Figure 4:
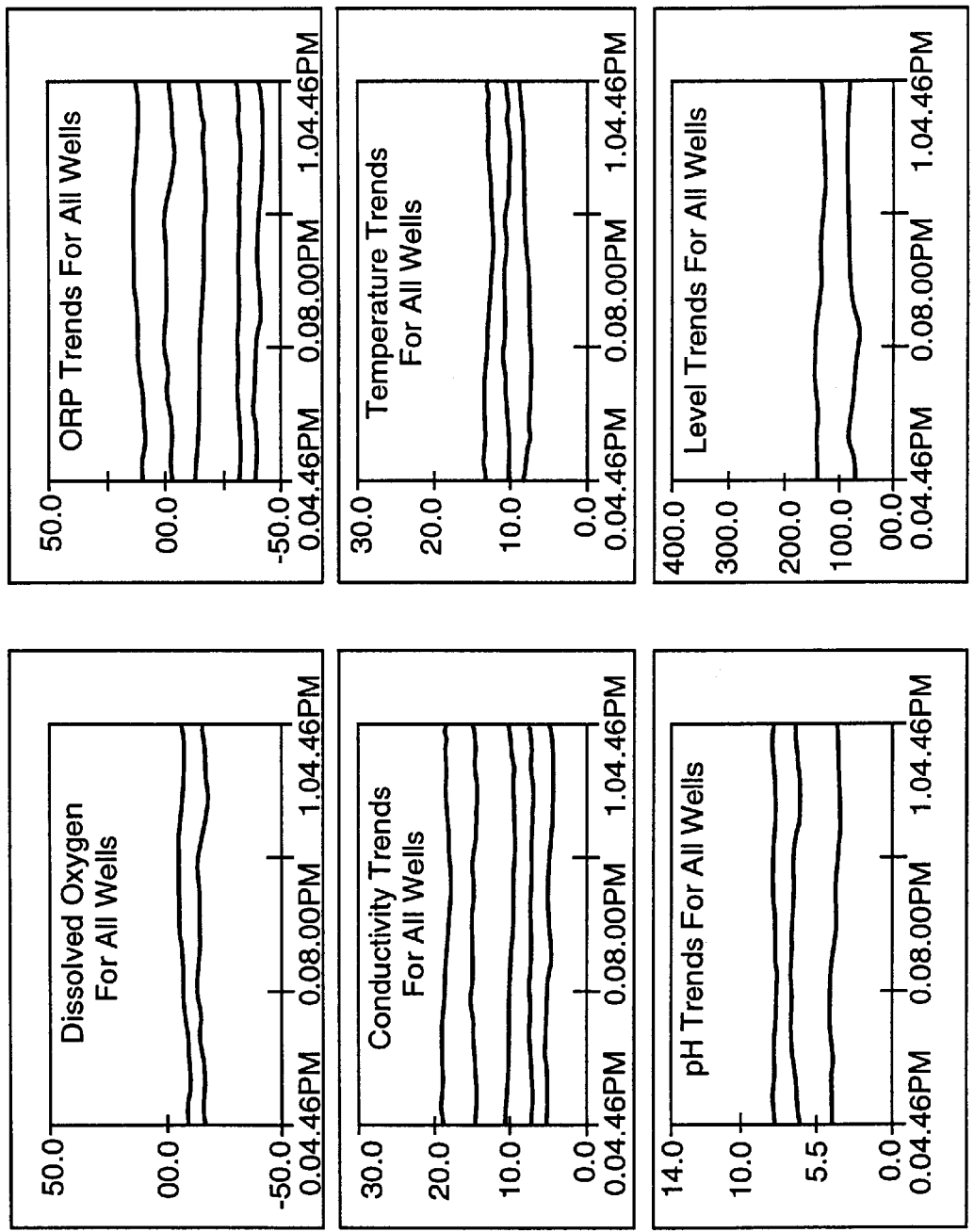
Figure 5:
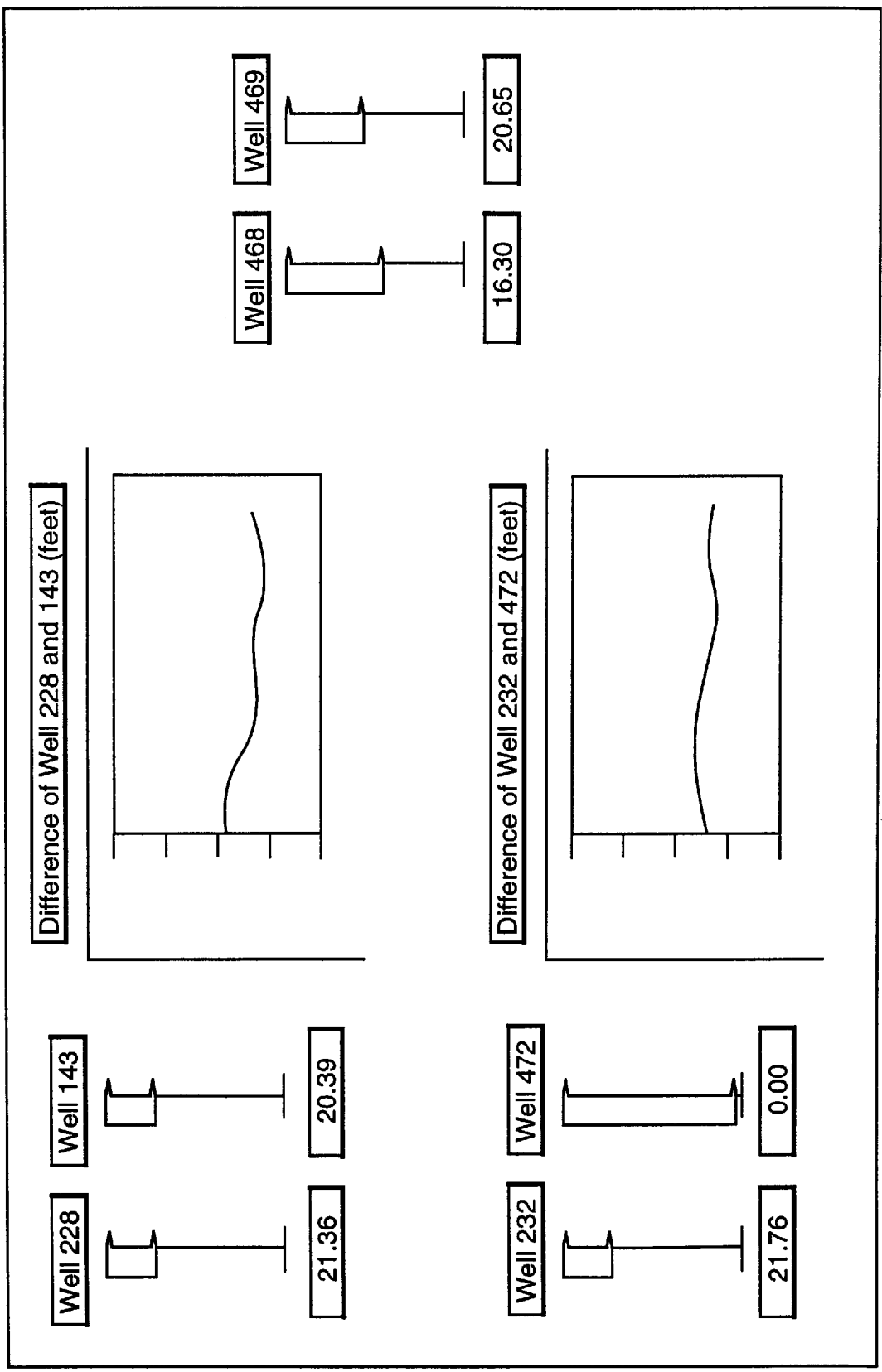

A report 60 can be customized by a user to present immediate electronic information in understandable, easy to interpret views. FIGS. 3–5 are exemplary formats for reports 60. FIG. 3 illustrates a report format 61 in which the data typically provides trends for all wells at a single remediation site over an extended period of time. The reports can be easily accessed, for example over the Internet. The graphs typically provide data for dissolved oxygen, conductivity, pH, ORP (oxidation reduction potential), temperature, and water level for all wells. These graphs and data are merely exemplary and are not meant to limit the invention in any way. FIG. 4 illustrates a report format 62 similar to the report illustrated in FIG. 3; however, the data are typically provided for the most recent two weeks. This format provides a user with detailed perspective of recent well activity. FIG. 5 is a further report format 63 that provides water elevation in wells. As illustrated, the format 63 provides data that can be arranged in many displays as desired by the user.

The monitoring system 1 can also incorporate components of a Global Positioning System (GPS) to enable a precise well location at a remediation site. When used in conjunction with a GPS, the monitoring system 1 provides the exact well location, for example, to a service or maintenance person visiting a well. The exact well location is often needed when a remediation site 100 has not been maintained, where undergrowth has obstructed a well, where snowfall has covered a well, and similar occurrences make location of a well difficult. The GPS can be tied in with satellites, for example, a satellite 75 and includes the data collection center 20, so that triangulation and exact well location is achieved through via the GPS and the monitoring system 1.

The monitoring system 1 can also include means capable of information statistical analysis for evaluating effectiveness, design of experiment methodology and quality control of the monitoring system 1. The means can be located in the control 22, the control 55, or both controls 22 and 55. The statistical analysis determines the process capability, where errors may possibly occur, effectiveness of individual feature performance, such as, but not limited to performance of the data control center, control 22, and communication link 30. The statistical analysis is also usable to determine sources of contamination, proximity of contamination to individual wells, flow rates of contamination, and other measurable information. Use of appropriate statistical analysis typically permits a user, such as a user that accesses the monitoring site 50, to evaluate and correct, if needed, components and operation of the monitoring system 1. The statistical analysis of information relies upon known information measurement and analysis procedures, such as, but not limited to, those described in *Six Sigma Productivity Analysis and Process Characterization*, Mikel J. Harry and J. Ronald Lawson. Addison-Wesley Publishing Co., 1992.

While various embodiments are described herein, it will be appreciated from the specification that various combinations of elements, variations or improvements therein may be made by those skilled in the art, and are within the scope of the invention.

What is claimed is:

1. A monitoring system to determine ground water contaminant characteristics in a well; the system comprising:
   a well module adapted to be disposed in the well at a ground water well site, the well module comprising a probe and at least one sensor that senses ground water contaminant characteristics, the well module being capable of transmitting signals concerning ground water contaminant characteristics and said well module adapted to have additional sensors added thereto;
   a data collection center capable of receiving well signals transmitted from the well module and generating information concerning ground water contaminant characteristics;
   a monitoring site that is remotely disposed from the data collection center;
   a remote water handling apparatus disposed at the ground water well site and linked to the data collection center, the remote water handling apparatus being capable of maintaining the ground water well site within compliance limits; and
   a communication link that interconnects the data collection center and the monitoring site to obtain the information concerning ground water contaminant characteristics and to transmit a control signal to the water handling, apparatus for directing an operation thereof;
   wherein the monitoring system further comprises a global positioning system that enables an accurate determination of a location of the well in the monitoring system, and the monitoring system transmits a user's action embodied in the control signal to the remote water handling apparatus in response to the received information concerning the ground water characteristics to maintain an operation of the ground water well site within compliance limits.

2. A system according to claim 1, wherein the communication link comprises a web connection.

3. A system according to claim 1, wherein the communication link comprises an Internet connection.

4. A system according to claim 1, wherein the communication link comprises at least one of:

a phone modem connection, radio communication connection, network communication connection, wireless communication system connections, cellular communication connection, satellite communication connection, web connection, and Internet connection, and combinations thereof.

5. A system according to claim 1, further comprising means for statistically analyzing and evaluating the monitoring system.

6. A system according to claim 1, wherein the data collecting center comprises a control.

7. A system according to claim 6, wherein the control comprises a computer.

8. A system according to claim 1, wherein the data collecting center comprises a transceiver.

9. A system according to claim 8, wherein the transceiver comprises at least one of an integrated antenna with the transceiver and an antenna that is separate from the transceiver.

10. A system according to claim 8, wherein the data collecting center further comprises a control.

11. A system according to claim 1, wherein the module further comprises a well transceiver and the fluid characteristics sensed by the at least one sensor are transmitted from the well transceiver and to the data collection center.

12. A system according to claim 11, wherein the well transceiver is in communication with the module by at least one of a hardwired connection and a wireless connection.

13. A system according to claim 12, wherein the wireless connection comprises at least one of a radio connection and a satellite connection.

14. A system according to claim 11, wherein the well transceiver comprises an antenna, the antenna comprises at least one of an integrated antenna with the well transceiver and a separate antenna from the well transceiver.

15. A system according to claim 1, wherein the monitoring site comprises a control that is adapted to output reports concerning the fluid characteristics.

16. A system according to claim 15, wherein the control provides report formats that provide real-time fluid characteristics.

17. A system according to claim 16, wherein the report formats comprise at least one of tables, graphs, charts, spreadsheets, and combinations thereof.

18. A system according to claim 15, wherein the control provides historical fluid characteristics.

19. A system according to claim 15, wherein the reports are automatically generated.

20. A system according to claim 15, wherein the reports are automatically generated at regular intervals.

21. A system according to claim 1, wherein the sensor comprises at least one of an in-situ sensor, vapor sensor, chemical sensor, fiber optics sensor, solid-state sensor, metal oxide sensor, and electrochemical sensor, and combinations thereof.

22. A system according to claim 1, further comprising a plurality of sensors to determine a plurality of fluid characteristics.

23. A system according to claim 1, wherein the fluid is groundwater and the well comprises a groundwater well.

24. A system according to claim 1, wherein the information comprises at least one of real-time information, historical information, and a combination of real-time and historical information.

25. A method of monitoring ground water contaminant characteristics of a well at a ground water well site using a well module in the well, the well module comprising a probe and at least one sensor, the method comprising:

sensing ground water contaminant characteristics with said well module;

transmitting signals concerning ground water contaminant characteristics from the well module to a data collection center;

receiving signals concerning ground water contaminant characteristics at the data collection center;

generating information concerning ground water contaminant characteristics at the data collection center;

obtaining information concerning the ground water contaminant characteristics at a monitoring site which is disposed remote from the data collection center;

determining an accurate location of each respective well by coordinating locations using a global positioning system; and transmitting a remote user's action embodied in a control signal to a water handling apparatus disposed at the remediation site, the water handling apparatus being capable of maintaining the ground water well site within compliance limits, the remote user's action being generated in response to the information concerning ground water characteristics received at the monitoring site for maintaining an operation of the ground water well site within compliance limits.

26. A method according to claim 25, wherein the step of obtaining information comprises accessing the information over at least one of web connections, phone modem connections, radio connections, network connections, wireless connections, cellular connections, satellite connections, web connections, and Internet connections, and combinations thereof.

27. A method according to claim 25, wherein the step of obtaining information comprises obtaining information via an Internet connection.

28. A method according to claim 25, wherein the data collecting center comprises a control and a transceiver, the method further comprises transmitting information from the transceiver and storing information in the control.

29. A method according to claim 25, further comprising a well transceiver, the well transceiver receiving information from the sensor and transmitting fluid characteristics as signals to the data collection center.

30. A method according to claim 29, further comprising a step of communicating between the well transceiver and the sensor by at least one of a hardwired connection and a wireless connection.

31. A method according to claim 30, wherein the step of communicating comprises at least one of communication by radio and satellite.

32. A method according to claim 25, further comprising statistically evaluating the monitoring method.

33. A method according to claim 25, wherein the monitoring site comprises a control, and the method comprises, outputting reports concerning the fluid characteristics.

34. A method according to claim 33, wherein the reports comprise tables, graphs, charts, spreadsheets, and combinations thereof.

35. A method according to claim 33, further comprising a step of providing historical data of fluid characteristics.

36. A method according to claim 33, wherein the step of outputting of reports is automatic.

37. A method according to claim 25, further comprising a step of selecting the sensor from a group comprising in-situ sensors, vapor sensors, chemical sensors, fiber optics sensors, solid-state sensors, metal oxide sensors, and electrochemical sensors, and combinations thereof.

38. A method according to claim 25, further comprising a step of providing two-way communication with the data collecting center and a user, the two-way communication permitting at least one of selection, activation and de-activation, modification, fine-tuning, manipulation, and resetting of at least one of the sensor, probe, and well module.

39. A method according to claim 30, wherein the well comprises a groundwater well and the fluid is groundwater, the method further comprises determining at least one groundwater characteristic selected from the group consisting of:
water quality parameters; groundwater level; contaminant content, impurities content, benzene content, toluene content, chlorinated solvents content, ethyl-benzene content, xylenes content, and combinations thereof.

40. A method according to claim 30, wherein the step of obtaining information comprises at least one of obtaining real-time information, historical information, and a combination of real-time and historical information.

41. A monitoring system to determine ground water contaminant characteristics in a plurality of wells; the system comprising:
a well module adapted to be disposed in each of the wells at a remediation site, the well module comprising a probe and at least one sensor that senses ground water contaminant characteristics, the well module being capable of transmitting signals concerning ground water contaminant characteristics and said well module being adapted to have additional sensors added thereto;
a data collection center capable of receiving well signals transmitted from the well module and generating information concerning ground water contaminant characteristics;
a monitoring site that is remotely disposed from the data collection center;
a remote water handling apparatus disposed at the remediation site and linked to the data collection center, the remote water handling apparatus being capable of maintaining the remediation site within compliance limits; and
a communication link that interconnects the data collection center and the monitoring site to obtain the information concerning ground water contaminant characteristics and to transmit a control signal to the water handling apparatus for directing an operation thereof;
wherein each well receives one said well module, each said well module transmitting information to the data collection center; the plurality of wells is arranged at the remediation site; and the monitoring system determines real-time contaminant characteristics at each well at the remediation site and transmits a user's action embodied in the control signal to the remote water handling apparatus in response to the received information concerning the ground water characteristics to maintain an operation of the remediation site within compliance limits.

42. A monitoring system to determine ground water contaminant characteristics in a well; the system comprising:
a well module adapted to be disposed in the well at a remediation site, the well module comprising a probe and at least one sensor that senses ground water contaminant characteristics, the well module being capable of transmitting signals concerning ground water contaminant characteristics and said well module adapted to have additional sensors added thereto;
a data collection center capable of receiving well signals transmitted from the well module and generating information concerning ground water contaminant characteristics;
a monitoring site that is remotely disposed from the data collection center;
a remote water handling apparatus disposed at the remediation site and linked to the data collection center, the remote water handling apparatus being capable of maintaining the remediation site within compliance limits; and
a communication link that interconnects the data collection center and the monitoring site to obtain the information concerning ground water contaminant characteristics and to transmit a control signal to the water handling apparatus for directing an operation thereof;
wherein the communication link is a two-way communication link between the data collection center and the monitoring site, the two-way communication link further permitting at least one of modification, fine-tuning, manipulation, and resetting of at least one of the sensor, probe, well module, and remote water handling apparatus; and the monitoring system transmits a user's action embodied in the control signal to the remote water handling apparatus in response to the received information concerning the ground water characteristics to maintain an operation of the remediation site within compliance limits.

43. A method of monitoring ground water contaminant characteristics of a plurality of wells at a remediation site using a well module in each of the wells, the well module comprising a probe and at least one sensor, the method comprising:
disposing the plurality of wells at the remediation site;
sensing ground water contaminant characteristics with said well module adapted to have a plurality of sensors from well to well at each of the plurality of wells;
transmitting signals concerning ground water contaminant characteristics from the well module to a data collection center;
receiving signals concerning ground water contaminant characteristics at the data collection center;
generating information concerning ground water contaminant characteristics at the data collection center;
obtaining information concerning the ground water contaminant characteristics across the remediation site at a monitoring site which is disposed remote from the data collection center;
determining real-time contaminant characteristics across the remediation site; and
transmitting a remote user's action embodied in a control signal to a remote water handling apparatus disposed at the remediation site, the remote water handling apparatus being capable of maintaining the remediation site within compliance limits, the remote user's action being generated in response to the information concerning ground water characteristics received at the monitoring site for maintaining an operation of the remediation site within compliance limits.

44. A method of monitoring ground water contaminant characteristics of a well at a remediation site using a well module in the well, the well module comprising a probe and at least one sensor, the method comprising:
sensing ground water contaminant characteristics with said well module adapted to have a plurality of sensors;

transmitting signals concerning ground water contaminant characteristics from the well module to a data collection center;

receiving signals concerning ground water contaminant characteristics at the data collection center;

generating information concerning ground water contaminant characteristics at the data collection center;

obtaining information concerning the ground water contaminant characteristics at a monitoring site which is disposed remote from the data collection center; and transmitting a remote user's action embodied in a control signal to a water handling apparatus disposed at the remediation site, the water handling apparatus being capable of maintaining the remediation site within compliance limits, the remote user's action being generated in response to the information concerning ground water characteristics received at the monitoring site for maintaining an operation of the remediation site within compliance limits;

wherein the method further comprising at least one of modifying, fine-tuning, manipulating, and resetting at least one of the sensor, probe, well module, and water handling apparatus.

* * * * *